(12) United States Patent
Novotny et al.

(10) Patent No.: US 6,210,685 B1
(45) Date of Patent: *Apr. 3, 2001

(54) ANTIGENIC PREPARATIONS AND ISOLATION OF SUCH PREPARATIONS

(75) Inventors: Pavel Novotny, deceased, late of Bromley (GB), by Jaroslava Novotny, executor; Juan Antonio Montaraz Crespo, Naucálpan (MX); Juraj Ivanyi, London (GB)

(73) Assignee: Medeva Pharma Limited, Leatherhead (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/334,690

(22) Filed: Jun. 17, 1999

Related U.S. Application Data

(60) Continuation of application No. 08/470,590, filed on Jun. 7, 1995, which is a division of application No. 08/210,458, filed on Mar. 21, 1994, now Pat. No. 5,648,080, which is a continuation of application No. 08/080,098, filed on Jun. 22, 1993, now abandoned, which is a continuation of application No. 07/830,989, filed on Feb. 4, 1992, now abandoned, which is a continuation of application No. 07/142,261, filed on Jan. 7, 1988, now abandoned, which is a continuation of application No. 06/894,435, filed on Jul. 30, 1986, now abandoned, which is a continuation of application No. 06/729,257, filed on May 1, 1985, now abandoned.

(30) Foreign Application Priority Data

May 12, 1984 (GB) .................................. 8412207

(51) Int. Cl.$^7$ .......................... A61K 39/10; A61K 39/02; A61K 39/00; C07K 1/00
(52) U.S. Cl. .................................. 424/254.1; 424/234.1; 424/240.1; 424/253.1; 424/184.1; 530/350; 530/825
(58) Field of Search .............................. 424/240.1, 254.1, 424/253.1, 184.1, 234.1; 530/350, 825, 412; 514/2

(56) References Cited

U.S. PATENT DOCUMENTS

| | | | |
|---|---|---|---|
| 3,141,824 | 7/1964 | Dahlstrom | 167/78 |
| 3,395,219 | 7/1968 | Millman | 424/92 |
| 3,465,078 | 9/1969 | Spiesel | 424/92 |
| 4,248,862 | 2/1981 | Ellwood et al. | 424/92 |
| 4,551,429 | 11/1985 | Greenspan | 435/68 |
| 4,705,686 | 11/1987 | Scott et al. | 424/92 |
| 5,101,014 | 3/1992 | Burns et al. | 530/350 |
| 5,237,052 * | 8/1993 | Novotny | 530/350 |
| 5,276,142 | 1/1994 | Gotto | 53/413 |
| 5,438,120 | 8/1995 | Novotny | 530/350 |
| 5,444,159 | 8/1995 | Jackson | 530/412 |
| 5,648,080 * | 7/1997 | Novotny | 424/254.1 |
| 5,667,787 | 9/1997 | Jackson | 424/253.1 |
| 5,885,586 | 3/1999 | Eckhardt et al. | 424/240.1 |
| 5,885,587 | 3/1999 | Eckhardt et al. | 424/240.1 |
| 5,895,655 | 4/1999 | Eckhardt | 424/240.1 |
| 5,897,867 | 4/1999 | Eckhardt | 424/240.1 |
| 6,048,700 * | 4/2000 | Novotny et al. | 435/7.1 |

FOREIGN PATENT DOCUMENTS

| | | |
|---|---|---|
| 2823750 | 5/1985 | (DE) . |
| 0 047 802 B1 | 3/1982 | (EP) . |
| 0 162 639 A3 | 5/1985 | (EP) . |
| 0 272 174 | 6/1988 | (EP) . |
| 0 336 736 A1 | 10/1989 | (EP) . |
| 0 437 687 A2 | 7/1991 | (EP) . |
| 0 462 534 A2 | 12/1991 | (EP) . |
| 0 527 753 B1 | 2/1993 | (EP) . |
| 0 471 726 B1 | 1/1997 | (EP) . |
| 0 267 998 A1 | 5/1998 | (EP) . |
| 2047886 | 3/1971 | (FR) . |
| 2014452 | 8/1979 | (GB) . |
| 1601870 | 11/1981 | (GB) . |
| 2083358 | 3/1982 | (GB) . |
| 5750925 | 3/1982 | (JP) . |
| WO 90/13313 | 11/1990 | (WO) . |
| WO 91/15505 | 10/1991 | (WO) . |
| WO 91/15571 | 10/1991 | (WO) . |

OTHER PUBLICATIONS

Idigbe et al. *J. Med. Microbiol.* 14: 409–418, 1981.*
Stenson et al. *Infect. Immun.* 63: 3780–3789, 1995.*
Airaksinen et al., *Biotechnological Letters*, 13(5):305–310 (1991).
Brennan et al., Abstract B–2, Annual Meeting of American Society of Microbiology, p. 30, (1988).
Brownlie et al., *Microbial Pathogenesis*, 1988, 4:335–344.
Burns et al., *Chemical Abstracts*, 112, p. 395, Abstract No. 1048386b (19$^{th}$ Mar. 1990).
Charles et al., *Eur. J. Immunol.*, 21:1147–1153 (1991).
Charles et al., *Research in Microbiology*, 144(9):681–690 (1993).
Glaser et al., *EMBO J.*, 12:3997–4004 (1988).
Gould–Kostka et al., Abstract B–126, Annual Meeting of the American Society of Microbiology, p. 51, 1989).
Gould–Kostka et al., *FEMS Microbiol. Letters*, 67:285–290 (Mar. 1990).
Ladant et al. *The Journal of Biological Chemistry*, 261:16264–16269 (1986).
Makoff et al., *Bio/Technology*, 8:1030–1033 (Nov. 1990).
Makoff et al., *Nucleic Acids Research*, 19(9):2417–2421 (1991).
Mooi et al., *Infection and Immunity*, 66(2):670–675 (1998).
Nara et al., *The Journal of Biological Chemistry*, 264:19308–19312 (1989).
Oxer et al., *Nucleic Acids Research*, 19(11):2889–2992 (1991).

(List continued on next page.)

*Primary Examiner*—Lynette R. F. Smith
*Assistant Examiner*—S. Devi
(74) *Attorney, Agent, or Firm*—Nixon & Vanderhye P.C.

(57) ABSTRACT

The present invention provides novel antigenic preparations comprising proteinaceous material associated with adenylate cyclase activity in cultures of *B. pertussis*, the said preparations being useful as components of acellular whooping cough vaccines. The invention further provides methods for the isolation of such antigenic preparations.

6 Claims, No Drawings

OTHER PUBLICATIONS

Pagliaccia et al., *Arch Microbiol.*, 168:437–440 (1997).
Palczewski et al., *The Journal of Biological Chemistry*, 263:14067–14073 (1988).
Pazirandeh et al., *The Journal of Biological Chemistry*, 264:18195–18201 (1989).
Pizza et al., *Science*, 246:497–500.
Scopes, *Analytical Biochemistry*, 165:235–246 (1987).
Strugnell et al., *Infection and Immunity*, 60(10), 3994–4002 (1992).
Swarup et al., *Biochem. J.*, 251:569–576 (1998).
Tuomanen et al., *Develop. Biol. Standard*, 1985, 61:197–204.
Vose, abstract of Lecture of $1^{st}$ Dec. 1989, J. Med. Microbiol., vol. 35, p. 187 (1991).
Weiss et al., *Ann. Rev. Microbiol.*, 40:661–686 (1986).
Weiss et al., *Dev. Biol. Stand.*, 61:11–19 (1985).
Weiss et al., *Infect. and Immun.*, 57(12):3757–3764 (1989).
Bulletin 1107 from Bio–Rad.
Catalog of Sigma Chemical, pp. 1750–1763 (1996).
Guide to Protein Purification ($2^{nd}$ Apr. 1990) Methods in Enzymology, vol. 182, edited by Deutscher.
Preliminary Programme of meeting held on $1^{st}$ Dec. 1989 at the National Institute for Biological Standards and Control, Potters Bar, UK.
Protein Purification Methods, A Practical Approach, edited by Harris and Angal, Oxford University Press (1989).
Betsou et al., Infection and Immunity, 63(9):3309–3315 (1995).
Monneron et al., Biochemistry, 27:536–539 (1988).
Complaint of Plaintiff Evans Medical Ltd., filed Feb. 10, 1995.
Amended Complaint of Plaintiff Evans Medical Ltd., filed Feb. 23, 1995.
Original Answer and Couterclaim of Defendant, American Cyanamid Company, filed Apr. 14, 1995.
Reply of Evans Medical Ltd. to Counterclaim of Defendant American Cyanamid Co., files May 4, 1995.
Second Amended Complaint of Plaintiffs' Evans Medical Ltd. and Medeva PLC, filed Sep. 18, 1996.
Answer and Counterclaim of Defendant, American Cyanamid Co., filed Sep. 26, 1996.
Original Answer and Counterclaim of Defendant, Takeda Chemical Industries, Ltd., filed Sep. 26, 1996.
Reply of Evans Medical Ltd. and Medeva PLC to Counterclaim of American Cyanamid Company, filed Oct. 16, 1996.
Reply of Evans Medical Ltd. and Medeva PLC to Counterclaim of Takeda Chemical Industries, Ltd., filed Oct. 16, 1996.
Third Amended Complaint of Plaintiffs Evans Medical Ltd. and Medeva PLC, filed Apr. 30, 1997.
Answer to Third Amended Complaint and Amended Counterclaim of Defendant American Cyanamid Co., filed Jul. 9, 1997.
Answer to Third Amended Complaint and Amended Counterclaim of Defendant, American Home Products Corp., filed Jul. 9, 1997.
Answer to Third Amended Complaint and Amended Counterclaim of Defendant Takeda Chemical Industries, Ltd., filed Jul. 9, 1997.
Reply of Plaintiffs to Amended Counterclaim of Defendant Takeda Chemical Industries, Ltd., filed Jul. 23, 1997.
Reply of Plaintiffs to Amended Counterclaim of Defendant American Cyanamid Co., filed Jul. 23, 1997.
Reply of Plaintiffs to Amended Counterclaim of Defendant American Home Products Corp., filed Jul. 23, 1997.
Fourth Amended Complaint of Plaintiffs Evans Medical Ltd. and Medeva PLC, filed Aug. 14, 1997, 1997.
Answer to Fourth Amended Complaint and Second Amended Counterclaim of Defendant Takeda Chemical Industries, Ltd., filed Sep. 3, 1997.
Answer to Fourth Amended Complaint and Second Amended Counterclaim of Defendant American Cyanamid Co., filed Sep. 3, 1997.
Answer to Fourth Amended Complaint and Second Amended Counterclaim of Defendant American Home Products Corp., filed Sep. 3, 1997.
Reply to Plaintiffs to Second Amended Couterclaim of Defendant American Cyanamid Company, filed Sep. 11, 1997.
Reply to Plaintiffs to Second Amended Counterclaim of Defendant American Home Products Corporation, filed Sep. 11, 1997.
Reply of Plaintiffs to Second Amended Counterclaim of Defendant Takeda Chemical Industries, Ltd., filed Sep. 11, 1997.
Index to Plaintiffs' Liability Deposition Exhibits.
Index to Defendants' Liability Deposition Exhibits.
Index of Deposition Transcripts, Deposition Transcripts included therein and cited Deposition Exhibits.
Pleading Index (27 volumes).
Report of Dr. William L. Dean pursuant to Rule 26(a)(2)(B), Federal Rules of Civil Procedure.
Direct Expert Report of Dr. Carine Capiau.
Rebuttal Expert Report of Dr. William L. Dean.
Rebuttal Expert Report of Dr. Carine Capiau.
Transcript of Pre–trial Hearing before Judge William C. Conner, United States District Court, Southern District of New York, May 26, 1998, in the matter of Evans Medical Ltd. et al. v. American Cyanamid Co. et al.
Plaintiffs' Memorandum in Support of Motion for Order Under 35 U.S.C. § 256 Correcting Inventorship.
Defendants' Memorandum in Opposition to Plaintiffs' Plaintiffs' Motion for Order Under 35 U.S.C. § 256 Correcting Inventorship.
Plaintiffs' Reply Memorandum in Support of Motion for Order Under 35 U.S.C. § 256 Correcting Inventorship.
Plaintiffs' Memorandum of Law in Support of Motion for Partial Summary Judgement Regarding Sufficiency of Deposit of Biological Material and Benefit of Foreign Priority.
Defendants' Memorandum in Opposition to Plaintiffs' Motion for Partial Summary Judgement Regarding Sufficiency of Deposit of Biological Material and Benefit of Foreign Priority.
Plaintiffs' Reply Memorandum Law in Support of Motion for Partial Summary Judgement Regarding Sufficiency of Deposit of Biological Material and Benefit of Foreign Priority.
Exhibits to Plaintiffs' Reply Memorandum Law in Support of Motion for Partial Summary Judgement Regarding Sufficiency of Deposit of Biological Material and Benefit of Foreign Priority.
Plaintiffs' Memorandum in Support of Motion for Partial Summary Judgement on Defendants' Affirmative Defense of Anticipation.

Exhibits to Plaintiffs' Memorandum in Support of Motion for Partial Summary Judgement on Defendants' Affirmative Defense of Anticipation.
Defendants' Memorandum in Opposition to Plaintiffs' Motion for Partial Summary Judgement on Defendants' Affirmative Defense of Anticipation.
Second Declaration of Dr. Marc Deitch.
Plaintiffs' Reply Memorandum in Support of Motion for Partial Summary Judgement on Defendants' Affirmative Defense of Anticipation.
Exhibits to Plaintiffs' Reply Memorandum in Support of Motion for Partial Summary Judgement on Defendants' Affirmative Defense of Anticipation.
Defendants' Book of Exhibits in Opposition to Plaintiffs' Summary Judgement Motions.
Plaintiffs' Memorandum in Opposition to Defendants' Motion for Summary Judgement on Noninfringement and/or for Markman Hearing.
Plaintiffs' Memorandum in Opposition to Defendants' Motion for Summary Judgement of Invalidity Based on Takeda Prior Art.
Exhibits to Plaintiffs' Memorandum in Opposition to Defendants' Motion for Summary Judgement of Invalidity Based on Takeda Prior Art.
Plaintiffs' Memorandum in Opposition to Defendants' Motion for Summary Judgement of Invalidty Based on the Monatarz Publication.
Plaintiffs' Memorandum in Opposition to Defendants' Motion for Summary Judgement of Invalidity for Failure to Comply with the Best Mode Requirement of 35 U.S.C. § 112.
Opinion and Order of Judge William C. Conner, United States District Court, Southern District of New York, Jun. 10, 1998, in the matter of Evans Medical Ltd. et al. v. American Cyanamid Co. et al.
Appeal Pleading Index (3 volumes).
Appeal Brief for Plaintiffs–Appellants, Evans Medical Ltd. et al.
Appeal Brief for Defendants–Cross Appellants, American Cyanamid Co. et al.
Reply Brief for Plaintiffs–Appellants, Evans Medical Ltd. et al.
Reply Brief for Defendants–Cross Appellants, American Cyanamid Co. et al.
Corrected Joint Appendix of Nonconfidential Exhibits, vol. I of II.
Corrected Joint Appendix of Nonconfidential Exhibits, vol. II of III.
Larsen et al., Acta Pathol. Microbiol. Immunol. Scand. 92: 271—277, Oct.*
Bernardini et al., Journ. Bact. 172:6274–6281, 1990.
Liljestrom et al., Mol. Gen. Genet., 188:184–189, 1982.
Tagliabue et al., Tokai J. Exp. Med., 13 Suppl.:253–257, 1988.
Chatfield et al., Vaccine, 7:495–498, 1989.
Corbel et al., Dev. Biol. Stand., 89:343–347, 1997.
Corbel et al., J. Med. Microbiol., 25:174–175, 1991.
Nicosia et al., Proc. Natl. Acad. Sci., 83:4631–4635, 1986.
Relman et al., Proc. Natl. Acad. Sci., 86:2637–2641, 1989.
Brown et al., Infection and Immunity, 55:154–161, 1987.
Robinson et al., Infection and Immunity, 40:523–528, 1983.
Munoz et al., Microbiol. Immunol., 33(4):341–355, 1989.
Roberts, et al., Molecular Microbiology, 5:1393–1404, 1991.

DeMagistris et al., J. Exp. Med., 168:1351–1362, 1988.
Pillemer, L., Proceedings of the Society for Experimental Biology and Medicine, 75:704–705, 1950.
References from Prosecution of USSN 08/450,336 (6 References) including: (1) (see EP 0 272 174 cited above under "Foreign Patent Documents") (2) Rappuoli, Rino et al., "Progress Towards The Development of New Vaccines Against Whopping Cough", Vaccine, vol. 10, Issue 14, 1992, pp. 1027–1032. (3) Sato, Hiroko et al., "Pertussiss Toxin as a Protective Antigen", Bacterial Vaccines, Edited by John B. Robbins, M.D. et al., Praeger, New York, pp. 349–357. (4) Robinson, A. et al., "Pertussis Vaccine: Present Status and Future Prospects", Vaccine, vol. 3, Mar. 1985, pp. 11–22. (5) Chazono, M. et al., "The Purification and Characterization of an Acellular Pertussis Vaccine", Journal of Biological Standardization, vol. 16, 1988, pp. 83–89. (6) Podda, Audino et al., "Phase I Clinical Trial of an Accellular . . . ", Vaccine, vol. 9, Oct. 1991, pp. 741–745.
Fernandez and Weiss, "Cloning and Sequencing of a *Bordatella pertussis* Serum Resistance Locus", Infection and Immunity 62(11):4727–4738 (1994).
Deposition Transcript for Hazel Sidberry, vol. 1, May 18, 1998 (86 pages).
Deposition Transcript for Arthur Ray Crawford, vol. 1, May 22, 1998 (122 pages).
Redhead, "Serum antibody responses to the Outer membrane proteins of *Bordetella pertussis*", Infect & Immunity, 44:724–729 (1984).
Moss et al., *Annal of Internal Medicine*, 101:653–666 (1984).
Hewlett et al., *The Journal of Infections Disease*, 136:5216–5219 (1977).
Taber's Cyclopedic Medical Dictionary pp. 827 & 1393.
English abstract No. 40872S for FR–2.047.886 (Mar. 1971).
English abstract No. 84–033077/06 for JP–A–58–222,032 (Jun. 1982).
English abstract No. 84–284448/46 for JP–A–59–063,183 (Oct. 1982).
English abstract No. 84–285037/46 for JP–A–58–175,439 (Mar. 1983).
Novotny et al., *Rec. Méed. Véet.*, 163:431–438 (1987) (French article with English abstract on p. 438).
Aoyama et al., *AJDC*, 143:655–659 (1989).
Brennan et al., *Infection & Immunity*, 56(12):3189–3195 (1988).
Brennan et al., Abstract No. 33 from the 5th International Symposium on Pertussis, held in Copenhagen, Denmark, Sep. 22–23, 1988 (1988).
Brennan et al., *Tokai J. Exp. Clin. Med.*, 13 (Suppl.):211–215 (1988).
Burnette, *Bio/Technology*, 8:1002–1005 (1990).
Burnett, *The Lancet*, 346:241 (1995).
Capiau et al., Proceedings of the 6th International Symposium on Pertussis, held in Bethesda, Maryland, USA 26–28th Sep. 1990, pp. 75–86 (1990).
Domenighini et al., *Mol. Microbiol.*, 4(5):787–800 (1990).
Eldering et al., *J. Bacteriol.*, 74:133–136 (1957).
Eldering et al., *J. Bacteriol.*, 93:1758–1761 (1967).
Gonzalez, *JAMA*, 248:22–23 (1982).
Gotto et al., *Infection & Immunity*, 61(5):2211–2215 (May 1993).
Gotto et al., Abstract in International Workshop on *Bordetella pertussis*, Aug. 18–20, 1988, Rocky Mountain Laboratories, Hamilton, Montana, USA (1988).

Guiso et al., Proceedings of the Sixth International Symposium on Pertussis, NIH, Bethesda, Maryland, USA, 26–28th Sep. 1990, pp. 207–211 (1990).
Hewlett et al., *Adv. Cyclic Nucl. Res.*, 9:621–628 (1978).
Imaizumi et al., *J. Clinical Microbiol.*, 17:781–786 (1983).
Kamiya & Nii, *Tokai J. Exp. Clin. Med.*, 13 (Suppl.):45–49 (1988).
Kimura et al., *AJDC*, 145:734–741 (1991).
Kobisch et al., *Infection & Immunity*, 58(2):352–357 (1990).
Kuno–Sakai et al., *Tokai J. Exp. Clin. Med.*, 13 (Suppl.):15–19 (1988).
Noble et al., *JAMA*, 257:1351–1356 (1987).
Novotny et al., *J. Biol. Standard.*, 3:11–29 (1975).
Novotny et al., *J. Med. Microbiol.*, 10:347–365 (1976).
Novotny et al., Abstract from International Symposium on Pertussis Evaluation & Research on Acellular Pertussis Vaccines at Shizuoka, Japan, Sep. 14–15, 1990 (1990).
Novotny et al., *Infection & Immunity*, 50(1):190–198 (1985).
Novotny et al., *Infection & Immunity*, 50(1):199–206 (1985).
Novotny et al., *J. Inf. Dis.*, 164:114–122 (1991).
Novotny et al., *Develop. Biol. Standard.*, 73:243–249 (1991).
Pittman, *Rev. Inf. Dis.*, 1:401–412 (1979).
Pittman, *Ped. Inf. Dis.*, 3:467–486 (1984).
Redhead, *Infection & Immunity*, 44(3):724–729 (1984).
Roberts et al., *Vaccine*, 10(1):43–48 (1992).
Rogel et al., *J. Biol. Chem.*, 266:3154–3161 (1991).
Romanos et al. *Vaccine*, 9:901–906 (1991).
Sato et al., *Lancet*, 1:122–126 (1984).
Sato et al., *Tokai J. Exp. Clin. Med.*, 13:79–88 (1988).
Sato & Sato, Proc. Sclavo Internatl. Conf. at Sienna, Italy, Ann. Sclavo 1–2:191–197 (1986).
Shahin et al., *J. Exp. Med.*, 171:63–73 (1990).
Shukuda, transcript of comments made at the Workshop on Acellular Pertussis Vaccines held Sep. 22–24, 1988, pp. 23–26.
Stainer et al., *J. Gen. Microbiol.*, 63:211–220 (1971).
Thomas et al., *J. Inf. Dis.*, 159(2):211–218 (1989).
Turco et al., *Infection & Immunity*, 42:27–32 (1983).
Anon., *Physicians Desk Reference*, pp. 1149–1151 (1994).
Anon., WHO Technical Report Series No. 800, Annex 2, "Requirements for Diphtheria, Tetanus, Pertussis and Combined Vaccines" (1990).
Anon., *Science*, 269:307 (1995).
Hewlett et al., *PNAS USA*, 73(6):1926–1930 (1976).
Novotny et al., Proceedings of the Third International Symposium on Pertussis, 99–123, 1979.
Endoh et al., *Microbiol. Immunol.*, 24(2):95–104 (1980).
Chemical Abstracts 96, 1982, 197728e.
Confer et al., *Science*, 217:948–950 (1982).
Chemical Abstracts 99, 1983, 170610k.
Imaizumi et al., *Infection and Immunity*, 41(3):1138–1143 (1983).
Sato et al., *J. Microbiol. Methods*, 1:99–109 (1983).
Weiss et al., *Infection and Immunity*, 42(1):33–41 (1983).
Chemical Abstracts 101, 1984, 18519q.
Moss et al., *Annals of Internal Medicine*, 101:653–666 (1984).
Weiss et al., *J. Infect. Dis.*, 150(2):219–222 (1984).
Beesley & Novotny, abstract submitted to Annual Histochemistry Meeting, Royal Microscopical Soc., U.K. Jan. 8, 1985.
Montaraz et al., *Infection and Immunity*, 47(3):744–751 (1985).
Novotny et al., Proceedings of the Fourth International Symposium on Pertussis, Geneva, Switzerland, 25–27 Sep. 1984, *Develop. Biol. Standard*, 61:27–41 (1986).
Hewlett et al "Soluble Adenylate Cyclase from the Culture Medium of *Bordetella pertussis*", *J. Bacteriology*, Aug. 1976, pp. 890–898.
Chemical Abstract 87:130, 172 (1977), "Hewlett et al. Adenyl Cyclase in *Bordetalla pertussis* vaccines", *J. Infect. Dis.*, 136 (Suppl.):216–219 (1977).
Manclark et al, *Bacterial Vaccine*, Germonier, ed. Chapter 3, pp. 72–75.
E. Hewlett et al., "Adenylate Cyclase Toxin from *Bordetella pertussis*", *J. Biol. Chem.*, 264(32):19379–19384 (1989).
Staden, *Nucleic Acids Research*, 10(9):2951–2961 (1982).
I.G. Charles et al., *Proc. Natl. Acad. Sci. USA*, "Molecular Cloning and characterization of protective outer membrane protein p. 69 from *Bordetella pertussis*", 86:3554–3558, 1989.
P. Glaser et al., "The calmodulin–sensitive adenylate cyclase of *Bordetella pertussis*: cloning and expression in *Escherichia coli*", *Molecular Microbiology*, 2(1):19–30 (1988).
Novotny et al., *The Journal of Infectious Diseases*, 164:114–22 (1991).
Proceedings of the Fourth International Symposium on Pertussis Attachment.
Redhead et al., *J. Med. Microbiol.*, 19:99–108 (1985).
*Evans Medical Ltd., Medeva PLC and SmithKline Beecham et al. v. American Cyanamid et al.*, 98–1446, –1459 (U.S. Court of Appeals for the Federal Circuit, decided Aug. 9, 1999).

* cited by examiner

ANTIGENIC PREPARATIONS AND ISOLATION OF SUCH PREPARATIONS

This is a continuation of Ser. No. 08/470,590, filed Jun. 7, 1995, pending, which is a division of Ser. No. 08/210,458, filed Mar. 21, 1994, now U.S. Pat. No. 5,648,080, which is a continuation of Ser. No. 08/080,098, filed Jun. 22, 1993, now abandoned, which is a continuation of Ser. No. 07/830,989, filed Feb. 4, 1992, now abandoned, which is a continuation of Ser. No. 07/142,261, filed Jan. 7, 1988, now abandoned, which is a continuation of Ser. No. 06/894,435, filed Jul. 30, 1986, now abandoned, which is a continuation of Ser. No. 06/729,257, filed May 1, 1985, now abandoned.

The present invention relates to antigenic preparations for use in acellular vaccines against *Bordetella pertussis*, and to a method for the isolation of such preparations.

*Bordetella pertussis* causes a serious and debilitating disease in humans, children being particularly susceptible, which is kept under control in the developed countries by large scale immunisation programmes. It has been found that immunisation is a very important factor in the reduction of the disease and that failure to vaccinate can lead to increased incidence of the disease. In practically all areas, immunisation is effected using a whole cell *B. pertussis* vaccine which has been found to be relatively effective in preventing the disease. However, it has been recognised that whole cell vaccines may suffer from several draw-backs. Thus, for example, in about 1 in every 10,000 children inoculated, clinical symptoms occur which may include fever, local reactions and persistent screaming. Further, it would appear that some batches of whole cell vaccine provide no protection at all while still being associated with the possibility of undesirable side-effects.

With the currently low occurrence of the disease in developed countries with immunisation programmes, the benefit/risk ratio is poorly defined, and many clinicians believe that the risks of inoculation outweigh the benefits gained by immunisation. As a result, many children are not inoculated and there is then a serious risk of a pandemic of whooping cough. Considerable research effort has, therefore, been directed toward the development of improved pertussis vaccines and especially acellular vaccines which lack the components associated with the toxic effects of the whole cell vaccines hitherto used whilst incorporating those components necessary to protect against the disease.

The search for a safer, effective, acellular *B. pertussis* vaccine has been hampered in the past by the paucity of information regarding the identity and mechanisms of action of the pathogenic, toxic and protective moieties of *B. pertussis* contained in the whole cell vaccines. Work has, therefore, been concentrated on isolating and purifying the 20 or more surface antigens of the *B. pertussis* organism and characterising their ability to induce immune reactions (see, for example, J. Am. Med. Soc., 248 (1) 22–23). Examples of antigens that have been suggested for investigation include lymphocytosis promoting factor (pertussis toxin/LPF) filamentous haemagglutinin (FHA), lipopolysaccharide (LPS), agglutinogens, dermonecrotic toxin (DNT), heat labile and heat stable toxins, polymorphonuclear leukocyte inhibitor factor, adenylate cyclase and other surface components (Pertussis Vaccine Workshop, Feb. 11, 1982, Bureau of Biologics, U.S.A.). Other proposed candidate antigens for investigation include tracheal cytotoxin and various outer membrane proteins.

An early extract vaccine was developed by L. Pillemer (Proc. Soc. Exp. Biol. Med. (1950) 75, 704–705) which was based on disrupted *B. pertussis* cells and found to provide protection but was not adopted commercially in view of the toxicity of the preparation.

Examples of more recent *B. pertussis* extract vaccines that have been suggested include those described in U.K. Patent Specification 2 083 358A (Takeda) involving removal of endotoxin from culture supernatants; French Patent Specification 2 047 886 (Institut Merrieux) involving extraction of a microbial suspension with an anionic surfactant; and Japanese Patent Specification 58-222032 (Teijin) which comprises a sub-unit protein based on pertussis toxin (LPF).

Much of the work carried out on acellular pertussis vaccines is concentrated on the possibility of basing such a vaccine on LPF. However, it is believed that most (if not all) of the adverse effects hitherto observed to be associated with pertussis vaccination are related to the toxin. In combination with tetanus or diptheria toxoid and LPS, it is able to induce experimental encephalopathy in susceptible mice (L. Steinman, et al. Nature (1982) 299, 738–740; Redhead et al., Workshop on *B. pertussis*, Nat. Instl. of Biol. Standards & Controls, Holy Hill, Hampstead, London, 1983). Thus, LPF may, possibly, be responsible for brain damage should such complications occur after vaccination.

It has now been discovered that certain proteinaceous material, associated with adenylate cyclase activity, as hereinafter described, found in the cultures of *B. pertussis*, is capable of providing protection against challenge by *B. pertussis* when administered to experimental animals. This discovery that the proteinaceous material usually associated with adenylate cyclase activity is a major protective antigen against *B. pertussis* permits the preparation of vaccine formulations comprising antigenic preparations which are free from, or contain reduced amounts of, other known *B. pertussis* components which may be responsible for the toxic side-effects demonstrated by whole cell vaccines.

The term 'proteinaceous material associated with adenylate cyclase activity (abbreviated to 'ACAP' hereinafter) is used herein to refer to proteinaceous material which is extracted together with adenylate cyclase activity when extraction of the adenylate cyclase activity is performed using an aqueous, acidic (pH3) solution of glycine (0.25 M). The ACAP as defined above may comprise the adenylate cyclase enzyme per se or a binding protein for the enzyme.

Adenylate cyclase activity was assayed by the method of Hewlett, E., and Wolff, J. (J. Bacteriol. (1976) 127, 89–898).

In a first feature of the present invention is provided a vaccine formulation for protection against *B. pertussis* which includes an antigenic preparation derived from *B. pertussis* comprising ACAP, optionally toxoided e.g. using formalin, gluteraldehyde or β-propiolactone, together with a pharmaceutically acceptable carrier therefor.

In more detail the ACAP may be detected by isoelectric focussing as two bands, one having an isoelectric point (pI) of, about 7.0, the other (diffuse) band having an isoelectric point of 7.2–7.4. Adenylate cyclase activity was associated almost entirely with the neutral band (pI=7.0) but monoclonal antibodies to ACAP bound both bands strongly.

The ACAP in the above-mentioned preparations generally has a relative molecular weight of about 67,000 to 73,000, particularly 69,000, and an isoelectric point of 7.0–7.4 under preparative conditions as described infra.

By "relative molecular weight" is meant the apparent molecular weight as determined by 12% (w/w) polyacrylamide gel electrophoresis and standard molecular weight markers. The molecular weight of the antigenic proteins of the invention may thus be conveniently determined by the techniques described by U.K. Laemmli, *Nature*, 1970, 227, 680–685. Convenient standard molecular weight markers include, for example, bovine serum albumin, chymotrypsinogen A and ribonuclease.

Amino acid analysis has also shown that ACAP contains an unusually high proportion of proline, such that the proline: glutamic acid ratio is about 1:1 and this feature serves to distinguish ACAP from other *B. pertussis* proteins. A further distinguishing characteristic of ACAP is the fact that it cannot be detected by radio-iodination of its tyrosine residues by either the Chloramine T or the Iodogen methods.

According to a preferred embodiment of the present invention the above-mentioned ACAP is proteinaceous material which is characterised as having one or more of the following properties:

(i) a ratio of proline to glutamic acid of substantially 1:1;
(ii) the tyrosine residues are not iodinatable;
(iii) substantially free from intracellular, *B. pertussis* material;
(iv) a relative molecular weight of 67,000 to 73,000;
(v) an isoelectric point of 7.0 to 7.4, and
(vi) being acid-labile below a pH of about 3.

The above-mentioned antigenic preparations for use in the vaccine formulations according to the invention may, if desired, contain minor quantities of other antigenic compounds, in addition to the ACAP, for example, materials obtained together with the ACAP extracted from the *B. pertussis* organism. Such materials may comprise fragments of LPS and LPF which, in view of their possible detrimental side-effects, require toxoiding, e.g. with formalin. The antigenic preparations are, however, preferably substantially free from other antigenic components.

Adenylate cyclase has been previously isolated from *B. pertussis* (E. L. Hewlett et al., J. Bacteriol, 127, 890–898 and Proc. Nat. Acad. Sci., U.S.A., 73, 1926–1930) but there has been no suggestion that this material represents a protective antigen against *B. pertussis*. According to the work of Hewlett et al., only about 20% of the total adenylate cyclase activity from the *B. pertussis* organism, representing about 0.5% of the total enzyme, was found in the culture supernatant, the remaining 80% being bound to cells. An extraction process is therefore required by which the ACAP can be obtained in high purity and yield, in order to afford sufficient quantities, on a commercial scale, of ACAP for use in the above-mentioned antigenic preparations. A major difficulty to be overcome with such an extraction process is that the ACAP, among other proteins, is bound, part of it very firmly, to the LPS back-bone of the outer membrane. In the past, detergents have generally been used for the solubilisation of the membrane in order to liberate its associated proteins. However, the use of detergents for the extraction of outer membrane proteins from *B. pertussis* organisms has been found to have the following disadvantages:

a) the outer membrane is solubilised to form micellar aggregates comprising mixtures of outer membrane proteins;
b) the outer membrane proteins may be damaged;
c) new antigens, which do not exist in the bacterium, may be created, and
d) the extracted material is usually found to be water-insoluble after the detergent is removed.

We have now discovered that in contrast to the use of detergents, extraction of *B. pertussis* organisms using regulated, mildly acidic conditions results in the extraction of substantially increased yields (about 40 × better than previously reported techniques) of adenylate cyclase from the outer membrane in a form which is water-soluble.

Thus, in an alternative aspect of the present invention is provided a method for the isolation of an antigenic preparation containing ACAP from *B. pertussis* which comprises treating a culture of *B. pertussis* cells with an aqueous amino acid buffer of pH 2.5–3.5, comprising a hypertonic concentration of said amino acid with respect to the cells, separating the cells from the resulting supernatant and isolating an antigenic preparation containing ACAP from the supernatant.

The buffer employed in the above-described method preferably provides a pH of about 3 and advantageously includes a mineral acid, preferably hydrochloric acid, as the acidic component of the buffer and either glycine or alanine as the amino acid. The treatment of the cells with the buffer is preferably effected at a temperature of 5 to 50° C., preferably 30 to 45° C., ideally 37° C., advantageously for 1 to 24 hours, preferably 10 to 20 hours with an amino acid concentration of 0.1–1 M, preferably 0.25 M. The ACAP is acid-labile and may be destroyed if the pH drops below 3 during extraction.

After incubation of the cells with the buffer, the cells are discarded and the supernatant obtained after centrifugation, e.g. at about 100,000 g (to remove all particulate matter), is, if desired, precipitated, e.g. using ammonium sulphate, cold ethanol or acetone. p The supernatant extract obtained has been tested in the Kendrick Test, as described below, and has been found to provide protection in mice against intracerebral challenge with *B. pertussis*. Control vaccines containing no adenylate cyclase activity were found to provide little or no protection against challenge with *B. pertussis*, suggesting that ACAP may, in fact, be the most important factor in immunity. Analysis of batches of non-protective whole-cell vaccine has also shown that non-protection tends to be associated with a lack of adenylate cyclase activity, further suggesting that ACAP may be the key antigen necessary for eliciting an immune response against *B. pertussis*.

The supernatant extract used in the Kendrick Test may, however, also contain the ACAP in small quantities complexed with other proteins including fragments of LPS, in which case, it may be desirable to purify further the material for use in the vaccine formulations according to the invention. Thus, for example, further purification may be effected by ion-exchange chromatography and/or by preparative isoelectro-focussing to eliminate complexed material. Alternatively, the two methods of purification may be combined, i.e. the material not retained by the DEAE gel (i.e. the non-complexed material) can be electrofocussed. The method of purification may also comprise chromatofocussing. After the above-described purification steps the ACAP may, if desired, be further purified, for example, by passing the material through an immunosorbent column containing an appropriate monoclonal antibody against the ACAP.

The antigenic preparations described above, including those prepared by the above-described method according to the invention, may be incorporated into a vaccine formulation for inducing immunity to whooping cough in man. For this purpose the antigenic protein may be presented in association with a pharmaceutically acceptable carrier or adjuvant.

Pharmaceutically acceptable carriers, in this instance, are liquid media suitable for use as vehicles to introduce the antigen into the patient. An example of such a carrier is saline solution. The antigenic protein may be in solution or suspended as a solid in the carrier.

The vaccine formulation may also comprise an adjuvant for stimulating the immune response and thereby enhancing the effect of the vaccine. Convenient adjuvants for use in the present invention include, for example, aluminium hydroxide and aluminium phosphate.

Conveniently the vaccine formulations are presented to contain a final concentration of antigenic protein in the range of from 0.01 to 5 mg/ml, preferably 0.03 to 2 mg/ml, most preferably 0.3 mg/ml. After formulation the vaccine may be incorporated into a sterile container which is then sealed and stored at a low temperature, for example 4° C., or may be freeze-dried.

In order to induce immunity in man to whooping cough one or more doses of the vaccine suitably formulated may be administered. It is recommended that each dose is 0.1 to 2 ml preferably 0.2 to 1 ml, most preferably 0.5 ml of vaccine. The present invention, in a further aspect provides a method for inducing immunity to whooping cough in man, comprising the administration of an effective amount of a vaccine formulation, as hereinbefore defined, to the host.

The present invention also includes the use of ACAP (as defined above) in the preparation of a vaccine for use in the induction of immunity to whooping cough in man.

The vaccines of the present invention may be administered by any conventional method for the administration of vaccines including oral and parenteral (eg. subcutaneous or intramuscular) injection. The treatment may consist of a single dose of vaccine or a plurality of doses over a period of time.

Vaccines according to the present invention may also comprise one or more other antigenic components such as, for example, suitably toxoided typhoid and diphtheria toxins, or other B. pertussis antigens, such as toxoided LPF, to reduce the likelihood of mutant strains of B. pertussis avoiding the concomitant immune response.

The following Examples serve to illustrate the invention:

EXAMPLE 1

Acid Glycine Hydrolysis and Preparation of Crude Outer Membrane Proteins

The cells were harvested ¾ of the way through exponential phase and spun down at 8000 g (Sorvall, GSA angle head) for 20 min at 4° C. The supernatant was siphoned off and the cells were immediately gently resuspended in distilled water to a density of 20–30 mg/ml dry weight of cells. One third of this volume of 1 M glycine-HCl buffer, pH 3.0, was added under gentle stirring to obtain a final concentration of 250 mM glycine. The glycine solution contained EDTA (to obtain 5 mM in the final mixture) to stop enzymatic activity. The pH was checked and, where necessary, re-adjusted to pH 3.0 using 1–2 M HCl. The mixture was gently stirred in a 37° C. water bath until the temperature equilibrated and then incubated overnight (18 hrs) at 37° C. (without stirring). The pH was then adjusted to 7.2–7.4 using 10 M NaOH, which was added slowly to avoid local excess. The cells were sedimented at 5000 g for 20 min at 5° C., the supernatant was siphoned off, cooled in an ice-water bath to 1–2° C. and 2 volumes of pre-cooled acetone (−20 to −40° C.) were slowly added to avoid the temperature rising above 1–2° C. The mixture was then kept at −20° C. for 3–5 hrs and the precipitate collected in a pre-cooled (−10° C.) angle head at 4000 g for 20 min. The supernatant was siphoned off and discarded. The sedimented precipitate was dissolved in ice-cooled distilled water to approximately ¹/₂₀ of the original volume of cell suspension. The solution was then freed of insolubles and vesicles by spinning at 50000 g for 90–120 min at 5° C. The supernatant was collected and kept frozen or freeze-dried. 1% w/v mannitol was added before freeze-drying. Forty to eighty mg protein was obtained per gram dry weight of cells.

EXAMPLE 2

(a) Separation of the Crude Outer Membrane Protein Preparations by DEAE-Trisacryl Chromatography A DEAE-Trisacryl column, 3×16 cm, was equilibrated with 0.025 M TRIS, 0.035 M NaCL buffer, pH 8.8, and the material obtained in Example 1 (up to 1 g of protein) dialysed against the equilibrating buffer and pumped at 60 ml/hour through the column. The fractions (99 drops per tube, ca. 5 ml) were combined in pools 1–13. Part of the total applied protein (approx. ¼) is not retarded by the gel bed and would be as a large peak. The retained material was then eluted using 0.1, 0.2, 0.3 and 1.0 M NaCl in 0.025 M tris buffer (pH 8.8). The fractions were pooled and applied to a SDS-PAGE slab to establish the separation of proteins. The ACAP was present in the material unretarded by the column, as shown by SDS-PAGE, but was also present in the retarded material eluted by 0.2 M NaCl.

(b) Preparative Flat Bed Isoelectrofocussing in Granulated Gel (IEF)

This was performed according to LKB recommendations (Application Note 198, LKB-Producter AB, Bromma, Sweden). A suspension of 4 g Ultrodex (LKB) and 5 ml of pre-blended Ampholine, pH 3.5–9.5 were suspended in distilled water to a final volume of 100 ml, poured onto a horizontal tray 10.8×24.3 cm and evaporated under a flow of air to the recommended limit. Layered strips of 3 paper wicks (LKB, 2117-106) soaked in 1:20 dilution of the same Ampholine in distilled water, were placed at each end of the tray. The material from Example 2a was embedded into the gel using an application template (2×9.4 cm) which was pressed into the gel at ⅓–¼ of the distance along its length from the anodic end, the enclosed gel removed, transferred to a 10 ml disposable syringe, suspended in 3 ml of the said material from Example 2a (containing up to 500 mg protein) and finally injected back into the empty space formed by its removal. The gel was then smoothed with a spatula where necessary and left to equilibrate for 20 min. Meanwhile, one paper wick was soaked in a 1:100 dilution of phosphoric acid (sp.gr. 1.75) and added to the strips at the anodic end, and another in 1 M NaOH and placed at the cathodic end. The tray support in the flat bed IEF apparatus (Pharmacia type FBE-3000) was cooled by running tap water (15° C.) during the run. The gel was run at a constant 8 watts.

The ACAP was detectable as two bands, one of pI 7.0, and the other (diffuse) band of pI 7.2–7.4. Adenylate cyclase activity was associated almost entirely with the central band (pI 7.0) but monoclonal antibodies to ACAP bound both bands strongly.

Using a metal template the gel bed was then divided into 30 parallel fields, the gel was scraped from each field using a spatula and transferred to test tubes containing 1 ml distilled water. The pH of each fraction was measured at this stage. The gel suspensions were then transferred into small plastic columns, eluted with 2 ml 0.2 M ammonium bicarbonate buffer, pH 7.0 and the gel-free eluates frozen (−40° C.).

(c) Analytical Isoelectric Focussing (i) The same procedure was was used as for 2(b) above but a 12% polyacrylamide gel in the presence of 8 M urea was used. The same results as for 2(b) were obtained.

(ii) The same technique, but using an agarose gel in the presence of 10% sorbitol, showed 4 immuno-reactive bands of pI 4.5 to 6.0. The band of pI 4.0 retained the majority of adenylate cyclase activity.

EXAMPLE 3

Purification of ACAP Using a Monoclonal Immunosorbent Column

Mouse ascitic liquid containing a monoclonal immunoglobulin specific for ACAP was precipitated at room temperature by the addition of 2 volumes of 27% w/v $Na_2SO_4$ and left to stand for 2–4 hrs before being sedimented (2000 g for 15 min). The hybridoma which secretes the monoclonal immunoglobulin was deposited under the Budapest Treaty at the European Collection of Animal Cell Cultures, Porton Down, United Kingdom on Jan. 5, 1990 under accession number 90010501. The sediment was redissolved and dialysed against PBS. Five hundred mg of this protein (UV determination) was coupled to 70 ml of packed CNBr-Sepharose CL48 following the manufacturer's instructions (Pharmacia). Sephadex G-50 (medium) was applied to a 500 mm×25 mm column to a bed height of 200 mm. After washing the column with elution buffer (0.2 M ammonium bicarbonate, pH 7.0, containing 0.01% Thiomersal) a 5 mm thick layer of No. 12 Ballotini glass beads was poured on top of the Sephadex bed. After further washing, the Immunosorbent gel was poured onto the Ballotini glass bead layer, this being separated from the Sephadex bed allowing for separation of both. The column was further washed with elution buffer, and finally another Ballotini glass bead layer was placed on top of the 100 mm high immunosorbent bed to protect the top of the column.

To separate the ACAP on the immunosorbent column, 180 ml of the unretained eluate from the DEAE-Trisacryl Separation (Example 2) containing 1 mg/ml protein (Lowry), was applied at 5° C. to the immunosorbent column at 0.25 ml/min, washed with elution buffer (0.2 M ammonium bicarbonate, pH 7, 0.01% w/v Thiomersal) and, after the base-line had stabilized, 50 ml 6 M Urea in elution buffer was applied to the column to elute the adsorbed material. The positioning of the immunosorbent material over a Sephadex G-50 bed allowed for the simultaneous separation of the protein from urea during the run.

EXAMPLE 4

Culture of *B. pertussis*

The defined medium used for growth of the organism was based on the formula of Steiner and Scholte (1971) as previously described (Novotny and Brookes, 1975). All cultures were grown at 36–37° C. The liquid cultures, in loosely capped shake flasks (500 ml conical flask with 200 ml medium), were inoculated with a culture grown for 48 hrs on Cohen-Wheeler medium with 2% agar and 5% horse blood and agitated to give a gas exchange rate of 20–40 $\mu M$ $O_2$/hr. Such liquid cultures were used to inoculate the medium in 5 liters or 70 liters all-glass fermentors, while the pH was maintained at 7.6 by the controlled addition of 2 M HCl and the dissolved oxygen saturation at 5–10% by impeller agitation. The cultures were harvested before the end of the exponential phase, i.e. after approximately 36 hrs incubation (Novotny and Cownley, 1978).

EXAMPLE 5

Kendrick Test

This was performed according to W.H.O. Requirements for Pertussis Vaccine using MF1 or NIH Mice (OLAC, category 3, free of most pathogens including *B. bronchiseptica*), weighing 14–16 g. The antigen, in 0.5 ml volumes, was inoculated intraperitoneally and comprised a top dilution and three four-fold serial dilutions. After two weeks the mice were challenged intracerebrally using the recommended challenge strain 18-323 (100–200 $LD_{50}$). The number of survivors in each group was used for calculation of the $ED_{50}$ and of the relative potency in respect to the British Pertussis Reference Vaccine 66/84 using a program of parallel line probit analysis. A comparative test was also performed using an FHA/LPF vaccine. The results are shown in Table 1.

TABLE 1

PROTECTIVE POTENCY OF BORDETELLA PERTUSSIS FRACTIONS IN THE MOUSE PROTECTION TEST AGAINST B. PERTUSSIS 18-323 INTRACEREBRAL CHALLENGE ("KENDRICK TEST")

| Material | $ED_{50}$ $\mu g$ | Relative potency I.U./$\mu g$ protein | 4 I.U. in $\mu g$ protein (= single human dose) |
|---|---|---|---|
| Crude glycine hydrol. of B. pertussis hydrolysed at 37° C. | 20 | 0.02 | 190 |
| Crude glycine hydrol. of B. pertussis, | | | |
| hydrolysed at 4° C. | 77 | 0.003 | 1333 |
| Hydrolysed at 37° C. | 20 | 0.011 | 363 |
| Hydrolysed at 53° C. | 149 | 0.001 | 4000 |
| B. pertussis immunopurified adenylate cyclase | 19 | 0.011 | 364 |
| FHA/LPF vaccine | 77 | 0.003 | 1333 |

EXAMPLE 6

Amino Acid Analysis of ACAP

The amino acid analysis was carried out using a Rank Hilger Chromaspek amino acid analyser. Samples were prepared by the addition of 250 $\mu l$ of 6 N HCl (diluted from BDH Aristar grade) containing 0.1% (w/v) phenol to the dried sample material in a thick-walled Pyrex test-tube (7.5×1.2 cm) Tubes were then drawn out in an oxygen-natural gas blow-torch flame in order to produce a narrow orifice. After freezing the contents in a solid $CO_2$-ethanol bath, each tube was connected via a manifold and trap to a high vacuum pump and left for ten minutes to remove air. The tubes were then sealed off and placed in an oven at 110° C. for hydrolysis. The hydrolysed samples were dried in a vacuum desiccator over sodium hydroxide pellets. The dried residue was dissolved in 250 $\mu l$ of amino acid analyser starting buffer for automated analysis.

The amino acid values shown in Table 2 are averages of the results obtained from duplicate 24, 48 and 68 hour hydrolyses except in the case of valine and isoleucine where the 68 hour hydrolysis values were used.

Values for cystine, cysteine and tryptophan could not be determined by this method.

TABLE 2

| | residues |
|---|---|
| Aspartic acid (+ Asparagine) | 48 |
| Threonine | 33 |

TABLE 2-continued

|  | residues |
| --- | --- |
| Serine | 33 |
| Glutamic acid (+ Glutamine) | 62 |
| Proline | 60 |
| Glycine | 77 |
| Alanine | 82 |
| Valine | 54 |
| Methionine | 4 |
| Isoleucine | 22 |
| Leucine | 50 |
| Tyrosine | 7 |
| Phenylalanine | 11 |
| Histidine | 13 |
| Lysine | 19 |
| Arginine | 37 |

EXAMPLE 7

Vaccine Formulations

Vaccines for use in immunisation may be prepared by conventional techniques with the following constituents:

a) Diphtheria, Tetanus and Pertussis Vaccine in Simple Solution

Each 1 ml of vaccine contains:

| Diphtheria Toxoid | >60 I.U. |
| --- | --- |
| Tetanus Toxoid | >120 I.U. |
| Pertussis Antigen according to the Invention | >0.363 mg |
| Sodium borate | <10.03 mg |
| Succinic acid | <3.10 mg |
| Thiomersal | 0.04–0.2 mg |
| Sodium chloride | <8.5 mg |
| Water | to 1 ml | b) Adsorbed Diphtheria, Tetanus and Pertussis Vaccine

The diphtheria, tetanus and pertussis components are adsorbed onto aluminium hydroxide gel by standard techniques.

Each 1 ml of vaccine contains:

| Diphtheria Toxoid | >60 I.U. |
| --- | --- |
| Tetanus Toxoid | >120 U.L. |
| Antigen according to the invention | >0.363 mg |
| Insoluble aluminium salts | <Equivalent to 0.093 mmols (2.5 mg) Al. |
| Sodium borate | <8.01 mg |
| Succinic acid | <2.48 mg |
| Thiomersal | 0.04–0.2 mg |
| Sodium chloride | <6.8 mg |
| Water | to 1 ml | c) Pertussis Vaccine

Each 1 ml of vaccine contains:

| Antigen according to the invention | >0.363 mg |
| --- | --- |
| Thiomersal | 0.04-0.2 mg |
| Sodium chloride | <8.5 mg |
| Water | to 1 ml |

What is claimed is:

1. *Bordetella pertussis* antigen useful for making a vaccine,
    wherein the antigen is characterized by (a) having a relative molecular weight of about 67,000 to 73,000 Daltons as determined by 12% (w/w) polyacrylamide gel electrophoresis and (b) binding to the monoclonal immunoglobulin secreted by the hybridoma deposited at the European Collection of Animal Cell Cultures, Porton Down, United Kingdom, under accession number 90010501, and
    wherein the antigen is in an amount effective to induce an immune reaction to said antigen in a patient.

2. The antigen of claim 1, wherein the antigen has a relative molecular weight of about 69,000 Daltons as determined by 12% (w/w) polyacrylamide gel electrophoresis.

3. The antigen of claim 1, wherein said antigen is substantially free of lipopolysaccharides.

4. The antigen of claim 1, wherein the antigen is purified.

5. The antigen of claim 2, wherein the antigen is purified.

6. The antigen of claim 2, wherein said antigen is substantially free of lipopolysaccharides.

* * * * *

UNITED STATES PATENT AND TRADEMARK OFFICE
CERTIFICATE OF CORRECTION

PATENT NO. : 6,210,685 B1
DATED : April 3, 2001
INVENTOR(S) : Novotny et al.

It is certified that error appears in the above-identified patent and that said Letters Patent is hereby corrected as shown below:

Column 1,
Line 41, replace "toward" with -- towards --.

Column 2,
Line 20, replace "Instl." with -- Inst. --.
Line 45, replace "89" with -- 890 --.

Column 4,
Line 25, after "acetone.", delete "p"

Column 6,
Line 10, replace "NaCL" with -- NaC1 --.
Line 16, after "be", insert -- collected --.
Line 65, delete the second occurrence of "was".

Column 7,
Line 20, replace "CL48" with -- CL4B --.
Line 26, replace "Immunosor-" with -- immunosor- --.

Column 8,
Line 27, delete the underlining.
Line 44, after "(7.5x1.2 cm)" insert -- . --.

Column 10,
Line 26 (claim 1, line 1), before "Bordetella pertussis", insert -- An acellular --.

Signed and Sealed this

Sixth Day of November, 2001

*Attest:*

*Attesting Officer*

NICHOLAS P. GODICI
*Acting Director of the United States Patent and Trademark Office*